US007829593B2

(12) United States Patent
Ohta et al.

(10) Patent No.: US 7,829,593 B2
(45) Date of Patent: Nov. 9, 2010

(54) GLUTAMINE-CONTAINING COMPOSITIONS AND A METHOD FOR INCREASING BLOOD FLOW USING SAME

(75) Inventors: Fumio Ohta, Kawasaki (JP); Tomo Takagi, Kawasaki (JP); Hiroyuki Sato, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/414,037

(22) Filed: Mar. 30, 2009

(65) Prior Publication Data

US 2009/0209614 A1    Aug. 20, 2009

Related U.S. Application Data

(63) Continuation of application No. PCT/JP2007/068988, filed on Sep. 28, 2007.

(30) Foreign Application Priority Data

Sep. 29, 2006  (JP)  .............................. 2006-266544

(51) Int. Cl.
*A61K 31/20* (2006.01)
*A61K 31/195* (2006.01)
(52) U.S. Cl. .................. 514/565; 514/560; 514/561
(58) Field of Classification Search .................. 514/560, 514/561, 565
See application file for complete search history.

(56) References Cited

U.S. PATENT DOCUMENTS

| 5,134,125 | A | 7/1992 | Hara et al. |
| 5,248,697 | A * | 9/1993 | Wilmore ..................... 514/563 |
| 5,658,895 | A | 8/1997 | Aoi et al. |
| 6,001,878 | A | 12/1999 | Van Leeuwen et al. |
| 6,291,525 | B1 | 9/2001 | Nissen |
| 6,346,264 | B1 | 2/2002 | White |
| 2002/0182162 | A1 | 12/2002 | Shahinpoor et al. |
| 2003/0018076 | A1 | 1/2003 | Fossel |
| 2006/0228396 | A1 | 10/2006 | Ohta et al. |
| 2007/0197392 | A1 | 8/2007 | Takeuchi et al. |

FOREIGN PATENT DOCUMENTS

| JP | 08-198748 | 8/1996 |
| JP | 09-241156 | 9/1997 |
| JP | 11-130669 | 5/1999 |
| JP | 2001-316256 | 11/2001 |
| JP | 2002-045122 | 2/2002 |
| JP | 2002-255827 | 9/2002 |
| JP | 2004-018483 | 1/2004 |
| JP | 2004-262878 | 9/2004 |
| JP | 2006-306865 | 11/2006 |
| WO | WO95/18608 | 7/1995 |
| WO | WO02/062329 | 8/2002 |

OTHER PUBLICATIONS

Bergana, M. M., et al., "NMR and MS Analysis of Decomposition Compounds Produced from N-Acetyl-L-glutamine at Low pH," J. Agric. Food Chem. 2000;48:6003-6010.
Biomedical Gerontology 2001;25(2):83-88.
Bode-Böger, S. M., et al., "L-arginine-induced vasodilation in healthy humans: pharmacokinetic-pharmacodynamic relationship," Br. J. Clin. Pharmacol. 1998;46:489-497.
Flynn, W. J., et al., "Intestinal Blood Flow is Restored with Glutamine or Glucose Suffusion after Hemorrhage," J. Surg. Res. 1992;52:499-504.
Folia Pharmacologica Japonica 2002;119:7-14.
Houdijk, A. P. J., et al., "Glutamine-enriched enteral diet increases splanchnic blood flow in the rat," Am. J. Physiol. Gastrointest. Liver Physiol. 1994;267:G1035-1040, with Abstract.
McPherson, R. W., et al., "Cerebral Blood Flow in Primates Is Increased by Isoflurame over Time and Is Decreased by Nitric Oxide Synthase Inhibition," Anesthesiology 1994;80:1320-1327.
Morikawa, E., et al., "L-arginine infusion promotes nitric oxide-dependent vasodilation, increases regional cerebal blood flow, and reduces infarction volume in the rat," Stroke 1994;25:429-435 (Abstract Only).
Pang, K. S., et al., "The Effect of Hepatic Blood Flow on Formation of Metabolites," Drug Metabolism and Disposition 1990;18(3):270-275.
Roth, E., "L-arginine-nitric oxide metabolism. Glutamine: a new player in this metabolic game?" Clin. Nutr. 1998;17:1-2.
Yarnitsky, D., et al., "Blood-brain barrier opened by stimulation of the parasympathetic sphenopalatine ganglion: a new method for macromolecule delivery to the brain," J. Neurosurg. 2004; 101:303-309.
International Search Report and Written Opinion of the International Searching Authority for PCT Patent App. No. PCT/JP2007/068988 (Dec. 11, 2007).

* cited by examiner

*Primary Examiner*—Raymond J Henley, III
(74) *Attorney, Agent, or Firm*—Shelly Guest Cermak; Cermak Nakajima LLP

(57) ABSTRACT

The present invention provides a glutamine-containing composition which functions to increase blood flow. Glutamine is present in the composition in an amount of 25 mg/kg body weight to 150 mg/kg body weight. By administering the composition to a subject in need thereof, the blood flow in the capillary vessels can be efficiently increased, while inhibiting any side effects such as low blood pressure. The present invention also provides food or feed containing the composition for increasing blood flow.

8 Claims, No Drawings

GLUTAMINE-CONTAINING COMPOSITIONS AND A METHOD FOR INCREASING BLOOD FLOW USING SAME

This application is a continuation of PCT/JP2007/068988, filed Sep. 28, 2007, which claims priority under 35 U.S.C. §119 to Japanese Patent Application No. 2006-266544, filed on Sep. 29, 2006, which are incorporated in their entireties by reference.

BACKGROUND OF THE INVENTION

1. Field of the Invention

The present invention relates to glutamine-containing compositions and methods for increasing blood flow using the same. Specifically, the present invention relates glutamine-containing compositions and methods for increasing blood flow in the capillary vessels of a subject. The glutamine-containing compositions can be formulated as pharmaceutical products, foods, beverages, animal feed, and the like.

2. Brief Description of the Related Art

Blood enables the transport of oxygen, nutrients, and chemical messengers such as hormones, waste products, and immune cells. Namely, substances are taken up by the blood from the lungs, digestive tract, and endocrine organs, and then they are transported to the entire body via the capillary vessels by the beating heart. Furthermore, waste products and the like are picked up by the blood through the capillary vessels throughout the entire body and finally excreted from the body via the lungs and kidneys, for example. Blood also helps in retaining heat in the body by continuous circulation while at a constant body temperature. Thus, blood flow in the capillary vessels is important for maintaining vital functions, but can be weakened when stresses occur, such as diseases including infectious disease, injury, fatigue, aging, and sudden environmental changes. For example, decreased blood flow in the brain may be related to cerebrovascular dementia and Alzheimer-type dementia, wherein the decreased blood flow causes deterioration of the vital functions (Biomedical Gerontology 2001: 25(2); 83-88). In addition, metabolism by the liver is influenced by the amount of blood flow. Accordingly, it is important to actively increase blood flow under such conditions so that heat retention in the body is increased and substances which actively enhance the vital functions are effectively transported by the increased blood flow.

Agents which have been used to increase blood flow include calcium antagonists, cellular respiration activators, anticonvulsants, in vivo enzymes, and the like.

Some of these agents were originally developed to reduce blood pressure. Such substances are designed to act on the blood vessels in every part of the body so that it is possible to not only increase blood flow in the capillary vessels, but also effect the systemic blood pressure. However, some of these in vivo enzymes, such as kallikrein, also can cause pain, for example. Therefore, it is strongly desirable to develop a method which is effective to increase blood flow and that is safe and easy to use.

It has been previously reported that arginine induces vasodilation. As the mode of action, vascular endothelial cells which contain nitric oxide synthases synthesize nitric oxide from arginine, which causes vasodilation. Externally administered arginine promptly synthesizes nitric oxide, which also produces vasodilation. However, dietary arginine does not usually have the same effect (Folia Pharmacologica Japonica 2002: 119; 7-14).

Although the effects of arginine when ingested have been widely reported, it has been conventionally thought that vasodilation caused by arginine results in an increase in blood flow as well as a lowering of blood pressure. For example, it has been reported, when 30 g or 6 g of arginine was intravenously administered to humans having a body weight of 78 kg on average, the 30 g of arginine lowered blood pressure and vascular resistance, while the 6 g of arginine did not have either effect (British Journal of Clinical Pharmacology 1998; 46: 489-497). In addition, other methods for increasing blood flow using arginine have been reported. In every such case, however, the dosage of arginine is very high, or the arginine must be combined with other compositions which alone act to increase blood flow, such as polyphenols (Anesthesiology 1994; 80: 1320-13, U.S. Patent No. 2002182162 and JP 2004-262878 A). Therefore, increasing blood flow using arginine by itself without concomitant reduction in blood pressure has never been reported.

SUMMARY OF INVENTION

It is an aspect of the present invention to provide a method of efficiently increasing blood flow in the capillary vessels.

A further aspect of the present invention is to provide a composition which can act to efficiently increase blood flow in the capillary vessels.

A further aspect of the present invention is to provide a pharmaceutical composition which comprises the composition described above.

A further aspect of the present invention is to provide a food composition which comprises the composition described above.

A further aspect of the present invention is to provide feed which comprises the composition described above.

The changes in blood flow in the capillary vessels after the administration of glutamine were carefully observed, and it was found that administration of glutamine within a certain dosage range increased blood flow in the capillary vessels, particularly the capillary vessels in the liver and the brain.

Namely, it is an aspect of the present invention to provide a method for increasing blood flow comprising administering to a subject in need thereof a composition comprising glutamine in an amount ranging from 25 mg/kg body weight to 150 mg/kg body weight per dose.

It is a further aspect of the present invention to provide the method as described above, wherein the amount ranges from 50 mg/kg body weight to 150 mg/kg body weight.

It is a further aspect of the present invention to provide the method as described above, wherein the glutamine is selected from the group consisting of L-glutamine, L-glutamine chlorides, and L-glutamine derivatives that can be metabolized to L-glutamine in vivo.

It is a further aspect of the present invention to provide the method as described above, wherein the composition is packed in a unit, and the unit comprises 1 to 27 g of glutamine.

It is a further aspect of the present invention to provide the method as described above, wherein the composition further comprises an amino acid selected from the group consisting of pyrrolidone carboxylic acids, pyrrolidone carboxylic acid salts, pyrrolidone carboxylic acid derivatives, and combinations thereof.

It is a further aspect of the present invention to provide the method as described above, wherein the ratio by mass of the glutamine to the amino acid is from 1:4 to 4:1.

It is a further aspect of the present invention to provide a method for preventing, alleviating, or treating dementia, cold constitution, shoulder stiffness, skin muddiness, impaired liver function, lowered immunity, and muscle fatigue comprising administering the composition as described above to a subject in need thereof.

It is a further aspect of the present invention to provide a composition for increasing blood flow comprising glutamine in an amount ranging from 25 mg/kg body weight to 150 mg/kg body weight.

It is further aspect of the present invention to provide a composition for increasing blood flow comprising glutamine in an amount ranging from 50 mg/kg body weight to 150 mg/kg body weight per a dose.

It is a further aspect of the present invention to provide a pharmaceutical composition comprising the composition as described above and a pharmaceutically acceptable carrier or diluent.

It is a further aspect of the present invention to provide a food comprising glutamine in an amount ranging from 25 mg/kg body weight to 150 mg/kg body weight per a dose.

It is a further aspect of the present invention to provide a feed composition comprising the composition described above.

According to the present invention, the blood flow in the capillary vessels can be increased effectively while inhibiting side effects such as low systemic blood pressure. In particular, the invention makes it possible to increase blood flow in the capillary vessels of the liver and the brain.

DETAILED DESCRIPTION OF THE PREFERRED EMBODIMENTS

The term "glutamine" includes L-glutamine, L-glutamine halides, preferably L-glutamine chlorides, and L-glutamine derivatives which can be promptly metabolized to L-glutamine in vivo. The L-glutamine derivatives may be in the form of esters, amides, peptides, proteins, pyrrolidone carboxylic acids, and the like, as well as peptides which contain L-glutamine as a constituent amino acid, for example. In particular, L-glutamine is preferable.

The amount of glutamine in the compositions ranges from 25 mg/kg body weight to 150 mg/kg body weight, preferably 50 mg/kg body weight to 150 mg/kg body weight per dose.

The amount of glutamine in the composition should be sufficient to increase the concentration of free glutamine in the blood plasma by 15 to 180 mg, preferably 25 to 180 mg, more preferably 50 to 180 mg, and yet more preferably 50 to 150 mg, per milliliter of blood plasma. A single dose of the composition may result in such an increase. The concentration of the free glutamine in the blood plasma can be determined by measuring the blood plasma 10 minutes after the administration of glutamine using an amino acid analyzer (the amino acid analyzer L8500 made by Hitachi, Ltd.).

When the blood flow increases by 20% or more relative to the blood flow before administrating the composition, the blood flow is considered to be increased. This is because the control can sometimes vary as much as 19%.

The composition may further include pyrrolidone carboxylic acid, and salts and derivatives thereof, and combinations thereof. Pyrrolidone carboxylic acid, and its salts or derivatives thereof help in the cell uptake of arginine (JP 2004-18483 A). This results in increased production of nitric oxide in the endothelial cells, which may further increase blood flow by the action of glutamine as described herein. Glutamine may be used in combination with glutamic acid, since glutamic acid can be converted to pyrrolidone carboxylic acid in an aqueous solution (Journal of Agricultural and Food Chemistry 2000; 48: 6003-6010).

The pyrrolidone carboxylic acid, and the salts or derivatives thereof, are preferably in L-form. The pyrrolidone carboxylic acids may form salts with alkali metals such as sodium and potassium, alkaline earth metals such as calcium, basic amino acids such as arginine and lysine, or amines such as triethanolamine. The pyrrolidone carboxylic acids may also form derivatives with alcohols and may be in the form of acid anhydrides, peptides, proteins, and the like. Particularly, sodium salt is preferable.

The glutamic acid includes L-glutamic acid and peptides containing L-glutamic acid as a constituent amino acid. The glutamic acids may form salts with alkali metals such as sodium and potassium, alkaline earth metals such as calcium, basic amino acids such as arginine and lysine, or amines such as triethanolamine. The glutamic acid may also form derivatives with alcohols and may be in the form of acid anhydrides, peptides such as wheat gluten hydrolysate, proteins such as wheat gluten. Particularly, L-glutamic acid is preferable.

Amino acids such as pyrrolidone carboxylic acid, and salts and derivatives thereof, can be administered in combination with glutamine. The dosage of such amino acids is not particularly limited, but may be preferably 6.25 mg/kg body weight to 600 mg/kg body weight, and more preferably 25 mg/kg body weight to 300 mg/kg body weight in a single dose.

The ratio by mass of glutamine to such amino acid(s) in the composition may be from 1:4 to 4:1, and more preferably from 1:2 to 2:1. It is preferable that the composition contain glutamine and the amino acid(s) in the above-stated ratio, because the volume of blood flow significantly increases.

The composition can preferably be used for preventing, alleviating, or treating cerebrovascular dementia, Alzheimer-type dementia, shoulder stiffness, cold constitution, skin muddiness, muscle fatigue, impaired liver function, lowered immunity, and the like. The increased blood flow can prevent, alleviate, or cure dementia, cold constitution, shoulder stiffness, skin muddiness, or muscle fatigue, as reported in Biomedical Gerontology 2001: 25(2); 83-88, Bulletin of Yamanashi Medical College 1999: 16; 15, Nitto Denko Technical Report 1992: 30, 1, JP 2002-255827 A, and JP 2001-316256 A. In addition, it is generally known that the administration of glutamine does not induce a lowering of the blood pressure (Journal of Surgical Research 1992: 52; 499). The composition described herein can effectively increase blood flow especially in the capillary vessels, and particularly those in the skin, spleen, liver, heart, and brain, while inhibiting the lowering of the systemic blood pressure, and therefore, more effectively distribute blood flow in the body.

The composition can be prepared as a pharmaceutical composition, as well as an additive in foods, health foods, dietary supplements, nutritional compositions, feed for livestock or domestic animals, or the like. These food compositions should indicate on their packaging that they are useful for increasing blood flow. The dosage generally varies depending on body weight, health conditions, and the like of the subject ingesting the food compositions. When administering to adults, 4.5 to 27 g, more preferably 9 to 27 g of glutamine per day is a preferable dose. The compositions may be packed in any product form so that a unit of product contains 1 to 27 g of glutamine, for example, 1 g, 2 g, 3 g, 4 g, or 4.5 to 27 g. When the glutamine amount per unit is 1 g, 2 g, 3 g, 4 g or the like, a plurality of units may be administered daily.

The pharmaceutical composition may also contain pharmaceutically acceptable carriers or diluents, for example, cellulose derivatives (carboxymethyl cellulose, ethyl cellulose and the like), starches (potato starch, corn starch and the like), sugars (lactose, sucrose and the like), vegetable oils (peanut oil, corn oil, sesame oil and the like), polyethylene glycol, alginic acid, gelatin, talc, and the like. The pharmaceutical composition may be prepared in a variety of dosage forms, such as orally administered preparations, e.g., tablets, powders, pills, granules, capsules, syrups and the like; injections, e.g., subcutaneous injections, intravenous injections, intramuscular injections, epidural injections, subarachnoidal injections, and the like; external preparations, e.g., nasally administered formulations, transdermally administered formulations, ointments and the like; suppositories such as rectal suppositories, vaginal suppositories and the like; intravenous fluids and the like.

The pharmaceutical composition may further comprise other active ingredients which are typically used as pharmaceuticals, including agents for the central or peripheral nervous system, agents for the circulatory organs, hormone preparations, antihormone preparations, vitamin preparations, revitalizers, detoxicating agents, antitumor agents, antiallergic agents, crude drugs, Chinese herbal medicines, chemotherapeutic agents, biological preparations, diagnostic agents, and the like.

The pharmaceutical composition may be orally or parenterally administered via a route such as, for example, rectally or intravenously.

With respect to food compositions, nonconventional food forms including supplements and the like are included, as well as conventional food forms. Food compositions can be prepared in a conventional manner by the addition of appropriate additives. Examples of such additives include any ingredients which are typically used in health food products, such as fruit juice to adjust and enhance the taste, dextrin, cyclic oligosaccharides, sugars (fructose and glucose syrup, sucrose), acidifiers, flavoring agents, green tea powder, and fats and oils, emulsifiers to improve the texture, collagen, whole milk powder, thickening polysaccharides, agar (employed for jelly-like beverage) and the like.

The food compositions may further comprise amino acids, vitamins, eggshell calcium, calcium pantothenate and other minerals, royal jelly, propolis, honey, dietary fibers, agaricus, chitin, chitosan, capsaicin, polyphenols, carotenoid, fatty acids, mucopolysaccharides, coenzymes, antioxidants and the like, and other ingredients typically used in the preparation of health food products.

The composition may also be used in feed compositions for mammals such as swine, bovines, sheep, canines, felines, mice, rats, monkeys, and the like. For example, a solid or liquid additive for use in feed can be prepared in accordance with methods which are conventionally known in the art.

The product form of the composition is not particularly limited, and includes those which are typically used for the delivery of amino acids. For oral administration, examples include powders, granules, tablets, liquids (e.g., beverages and jelly-like beverages) and sweets (e.g., chocolates), wherein a suitable excipient(s) is used, or a mixture of one or two kinds of the above amino acids. For intravenous administration, examples include infusion solutions and aqueous solutions, each containing one or two kinds of the above-mentioned amino acids, and amino acid powders that can be added before administration.

The blood flow in the capillary vessels is an important index for measuring the effect of administration of the composition described herein. Capillary blood flow can be measured using a laser Doppler blood flowmeter (FLO-N1, made by OMEGAWAVE, Inc.) or microspheres (Dye-Trak VII+, made by Triton Technology Ltd.).

EXAMPLES

The present invention will now be further illustrated with reference to the following non-limiting Examples.

Example 1

Determination of Changes in Blood Flow in Various Organs after Oral Administration of Glutamine to Rats (1) Summary of Experiment (a) Glutamine was given to rats and then the changes in blood flow in the capillary vessels of their various organs were determined.

(b) Male SD rats having a body weight of about 400 g were subjected to the experiment.

(c) The rats were anesthetized by pentobarbital, and catheters were placed in the left ventricle and the right femur of each rat. After the rats recovered from the anesthesia, glutamine was injected into the stomach of each rat through a feeding needle so that 50 mg/kg body weight of the amino acid was administered. Through the catheter located from the carotid artery to the left ventricle, yellow and red microspheres were each injected before and after the administration of the amino acid solution. The amounts of the microspheres which were distributed from the heart to the capillary vessels of each organ of the entire body were determined and compared to the blood flow of each organ before and after the administration of glutamine. For the control group, distilled water was administered.

(d) It was observed that glutamine increased the blood flow in the abdominal skin, spleen, liver, heart, and brain more than in other organs.

(e) From the above results, a significant increase in blood flow in the capillary vessels of the abdominal skin, spleen, liver, heart, and brain is shown in the rats to which 50 mg/kg of glutamine was administered. Therefore, when glutamine is administered according to the above protocol, the effect is significantly noticeable in the abdominal skin, spleen, liver, heart and brain.

(2) Details of Experiment (a) Composition administered in each group: shown in Table 1.

TABLE 1

| Administration Group | Composition | Dose of Total Amino Acids Dose of Glutamine |
| --- | --- | --- |
| Control group | distilled water | Total amino acids: 0 mg/kg Glutamine 0 mg/kg |
| Glutamine-administered group | | Total amino acids: 50 mg/kg Glutamine: 50 mg/kg |

(b) Operation: Catheters were inserted into the carotid and femoral arteries of the rats under anesthesia, the microspheres were injected via these catheters, and blood samples were taken.

(c) Determination of blood flow: Immediately before and after the administration of glutamine, which lasted 30 minutes, yellow and red microspheres were each injected into the left ventricle of each rat through the catheter. After a sufficient interval after the second injection of the microspheres, the rats were euthanized. The muscles, alimentary canals, liver, kidneys, spleen, heart, brain, fat tissue, and abdominal skin were extracted. The microspheres which had collected in each organ were removed and the change in the ratio of the blood flow was calculated from the amounts of microspheres present in each organ.

(d) Experimental results: The change in blood flow observed in the glutamine administration test is shown in Table 2.

TABLE 2

Change in blood flow after administration of amino acid, calculated on the basis of 100% blood flow before administration

|  | Control Group (%) | Glutamine-Administered Group (%) |
|---|---|---|
| Gastrocnemius | 94 | 105 |
| Soleus | 91 | 146 |
| Abdominal skin * | 94 | 146 |
| Dorsal skin | 97 | 154 |
| Fat tissues | 90 | 137 |
| Kidney | 105 | 113 |
| Spleen * | 90 | 146 |
| Duodenum | 100 | 136 |
| Liver * | 86 | 226 |
| Heart * | 111 | 259 |
| Brain * | 109 | 163 |

The organs labelled with an "*" indicate where the increase in blood flow was more noticeable than in other organs in the glutamine-administered group.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A method for increasing blood flow comprising administering to a subject in need thereof a composition comprising glutamine in an amount ranging from 25 mg/kg body weight to 150 mg/kg body weight per dose.

2. The method of claim 1, wherein the amount of glutamine ranges from 50 mg/kg body weight to 150 mg/kg body weight per dose.

3. The method of claim 1, wherein the glutamine is selected from the group consisting of L-glutamine, L-glutamine chlorides, and L-glutamine derivatives that can be metabolized to L-glutamine in vivo.

4. The method of claim 1, wherein, when the composition is packed in a unit, and the unit comprises 1 to 27 g of glutamine.

5. The method of claim 1, wherein the composition further comprises an amino acid selected from the group consisting of pyrrolidone carboxylic acids, pyrrolidone carboxylic acid salts, pyrrolidone carboxylic acid derivatives, and combinations thereof.

6. The method of claim 5, wherein the ratio by mass of the glutamine to the amino acid is from 1:4 to 4:1.

7. A method for increasing blood flow comprising administering a composition comprising glutamine as the active ingredient in an amount ranging from 25 mg/kg body weight to 150 mg/kg body weight per a dose.

8. A method for alleviating or treating a condition selected from the group consisting of dementia, cold constitution, shoulder stiffness, skin muddiness, muscle fatigue, impaired liver function, lowered immunity, and combinations thereof comprising administering to a subject in need thereof a composition comprising glutamine in an amount ranging from 25 mg/kg body weight to 150 mg/kg body weight per dose.

* * * * *